United States Patent
Lee et al.

(10) Patent No.: US 10,614,174 B2
(45) Date of Patent: Apr. 7, 2020

(54) SYSTEM AND METHOD FOR ADDING SURFACE DETAIL TO DIGITAL CROWN MODELS CREATED USING STATISTICAL TECHNIQUES

(71) Applicant: DENTSPLY SIRONA Inc., York, PA (US)

(72) Inventors: Jinho Lee, Belmont, MA (US); Alexander Yarmarkovich, Swampscott, MA (US); Kenneth Michael Flowers, Lexington, MA (US)

(73) Assignee: DENTSPLY SIRONA Inc., York, PA (US)

( * ) Notice: Subject to any disclaimer, the term of this patent is extended or adjusted under 35 U.S.C. 154(b) by 615 days.

(21) Appl. No.: 14/609,774

(22) Filed: Jan. 30, 2015

(65) Prior Publication Data

US 2016/0224690 A1 Aug. 4, 2016

(51) Int. Cl.

| | | |
|---|---|---|
| G06F 17/18 | (2006.01) | |
| G06F 17/50 | (2006.01) | |
| G16H 20/40 | (2018.01) | |
| A61C 13/00 | (2006.01) | |
| A61C 13/34 | (2006.01) | |

(52) U.S. Cl.
CPC .......... *G06F 17/50* (2013.01); *A61C 13/0004* (2013.01); *A61C 13/34* (2013.01); *G06F 17/18* (2013.01); *G16H 20/40* (2018.01)

(58) Field of Classification Search
None
See application file for complete search history.

(56) References Cited

U.S. PATENT DOCUMENTS

| 8,727,776 B2 | 5/2014 | Mehl |
| 2006/0063135 A1 | 3/2006 | Mehl |
| 2007/0154868 A1 | 7/2007 | Scharlack et al. |
| 2009/0246726 A1 | 10/2009 | Chelnokov et al. |
| 2010/0151404 A1 | 6/2010 | Wu et al. |
| 2011/0110575 A1 | 5/2011 | Banumathi et al. |
| 2011/0212419 A1 | 9/2011 | Schweiger |
| 2012/0171642 A1 | 7/2012 | Mehl |
| 2012/0320262 A1* | 12/2012 | Chung ............... H05B 33/0863 348/370 |
| 2013/0095448 A1 | 4/2013 | Phan et al. |
| 2014/0142902 A1* | 5/2014 | Chelnokov ............ A61C 7/002 703/1 |

(Continued)

OTHER PUBLICATIONS

Kanai et al. "Three-dimensional geometric metamorphosis based on harmonic maps" The Visual Computer (1998) 14: 166-176.*

(Continued)

*Primary Examiner* — Yanna Wu
(74) *Attorney, Agent, or Firm* — Dentsply Sirona Inc.

(57) ABSTRACT

Generating a crown model using a statistical method (such as k-means clustering, principal component analysis (PCA), or similar statistical methods) can result in a crown model that is missing sharpness details below the threshold of the statistical technique. A method is provided to add back the sharpness to the resulting model by combining a single full-featured example into the algorithms generating the statistical model. The end result is a crown model that is relatively simple to produce and manipulate in real time, yet maintains the anatomical sharpness of a natural tooth.

7 Claims, 5 Drawing Sheets

(56) References Cited

U.S. PATENT DOCUMENTS

2014/0229145 A1    8/2014   Van Lierde
2014/0379356 A1   12/2014   Sachdeva et al.
2015/0220683 A1*   8/2015   Chen ................ G06F 19/12
                                                                                703/2

OTHER PUBLICATIONS

Lemke et al.; "Generating geometrically deformable models by statistical shape modeling for computer aided dental restorations"; CARS; 2000; p. 841-845.
Lorenze et al.; "Generation of point based 3D statistical shape models for anatomical objects"; Computer Vision and Image Understanding; vol. 77 Issue 2; Feb. 2000; 32 pages; abstract.
MacQueen; "Some methods for classification and analysis of multivariate observations"; Proceedings of the $5^{th}$ Berkeley Symposium on Mathematical Statics and Probability; 1967; p. 281-297.
Kanungo et al.; "An efficient k-means clustering algorithm: Analysis and implementation"; IEEE Trans. Pattern Analysis and Machine Intelligence; vol. 24 No. 7; Jul. 2002; abstract; 36 pages.
Jones et al.; "Multidimensional Morphable Models: A Framework for Representing and Matching Object Classes"; Int'l Journal of Computer Vision; vol. 29 Issue 2; 1998; p. 107-131.
Blanz et al.; "A morphable model for the synthesis of 3D faces"; Proceedings of SIGGRAPH; Aug. 1999; p. 187-194.
Kanai et al.; "Three Dimensional Geometric Metamorphosis Based On Harmonic Maps"; The Visual Computer; vol. 14; 1998; p. 166-176.
Pighin et al.; "Synthesizing realistic facial expressions from photographs"; Proceedings of SIGGRAPH; 2006; 10 pages.

\* cited by examiner

SYSTEM AND METHOD FOR ADDING SURFACE DETAIL TO DIGITAL CROWN MODELS CREATED USING STATISTICAL TECHNIQUES

TECHNICAL FIELD

The invention relates to techniques for creating digital models of teeth and, more particularly, to a system and method for adding surface detail to digital crown models created using statistical techniques such as principal component analysis or k-means clustering.

BACKGROUND

In restorative dentistry, tooth shapes are typically generated based on a small set of sample tooth shapes called library teeth. Such library teeth are stored in tooth libraries and manipulated using 3D digital editing techniques that are equivalent to the physical processes of sculpting in wax and clay (i.e., by adding or removing material digitally from areas on the surface of the model in a manner analogous with adding or removing wax in physical modeling). This allows for a wide variation, but provides no means for assuring that the result continues to be a natural tooth shape. In particular, this approach has three primary problems:
1. It is a time consuming process.
2. It requires full dental knowledge and artistic skill to create a dentally appropriate tooth shape.
3. It does not prevent the result from not being an appropriate anatomical shape, should the knowledge and skill not be complete.

Other approaches for modeling natural tooth shape have been contemplated. First, one could create a completely parametric model of teeth. Unfortunately, a huge amount of parameters would be needed to correctly define a tooth. Even with such a model, it would be necessary to "imprint" fine detail onto the resulting parametric model. In any case, the model would be too time-consuming to use to design a specific tooth. On the other hand, a library of teeth could be morphed to create crown shapes. Those libraries naturally have the detail, but the libraries do not offer a way to automate the structurally important details. In a further approach, post processing of a statistical tooth model could be used to "imprint" a tooth-like pattern on the various regions of the final tooth shape. Unfortunately, such an approach results in a model that may have edge artifacts between the regions. Also, this process is computationally complex and error prone.

Other techniques are known in the art for generating a statistical tooth model using mathematical techniques known as principal component analysis (PCA). For example, U.S. Pat. No. 8,727,776 to Mehl discloses a method for producing denture parts or tooth restorations using electronic dental representation generating using PCA. PCA reduces the complexity of modeling an anatomical shape by looking at the characteristics of a set of samples and defining those elements of the sample that best characterize differences across the samples. A similar approach is described by Gurke in "Generating geometrically deformable models by statistical shape modeling for computer aided dental restorations," CARS 2000, Lemke, et al. editors (2000), which describes development of a tooth model based on a form of statistical shape analysis known as the Point Distribution Model including an analysis of the shape variance of a training set using eigenvectors and the definition of significant dental medical features. The weighted amounts of each eigenvector are added to the mean tooth shape of the training set to define the tooth model. The tooth model is used in an automatic CAD system for dental restorations. C. Lorenz, et al. also described in an article entitled "Generation of point based 3D statistical shape models for anatomical objects," Computer Vision and Image Understanding, Vol. 77, Issue 2, pages 175-191, February 2000, a technique for the generation of a statistical shape model for medical objects using PCA where a template shape is developed and all objects to be analyzed are fitted to the template. One of the benefits of these approaches is the processing speed improvements that can be gained by ignoring those aspects of the samples whose variation is not important in distinguishing the resulting tooth model. However, by ignoring these aspects for performance purposes, the resulting model appears less sharp than expected. A technique that provides improved sharpness is desired.

In any of these approaches, the results of creating a statistical model of anatomy can appear to be lacking detail. While the resulting model is structurally complete, customers can be put off by the lack of finished appearance. A technique is desired that delivers an effective statistical model of tooth anatomy while retaining the fine detail that customers expect.

K-means clustering is a known way to partition an N-dimensional data population into k sets on the basis of a sample. The mathematical basis for k-means clustering is described by MacQueen in an article entitled "Some Methods for classification and Analysis of Multivariate Observations," Proceedings of 5th Berkeley Symposium on Mathematical Statistics and Probability (1967). Spath also described a technique for k-means clustering in a text entitled "Cluster Dissection and Analysis: Theory, FORTRAN Programs, Examples," Translated by J. Goldschmidt New York: Halsted Press (1985). Kanungo, et al. also describe in an article entitled "An efficient k-means clustering algorithm: Analysis and implementation," IEEE Trans. Pattern Analysis and Machine Intelligence, Vol. 24, No. 7, pp. 881-892 (July, 2002), an implementation of k-means clustering using Lloyd's algorithm to determine the sample points in a data distribution.

Other approaches for partitioning data are known in the art. For example, Jones et al. describe in "Multidimensional Morphable Models: A Framework for Representing and Matching Object Classes," International Journal of Computer Vision, Volume 29, Issue 2, pp. 107-131 (1998), a multidimensional morphable model including a stochastic gradient descent algorithm that automatically matches a model to an image for use in computer vision. Blanz et al. similarly describe in an article entitled "A morphable model for the synthesis of 3D faces," Proceedings of SIGGRAPH 99, pages 187-194, August 1999, a technique for modeling textured 3D faces using a morphable face model by transforming the shape and texture of the examples in to a vector space representation.

It is desirable to create a digital model of teeth by creating a robust model of dental anatomy and then providing techniques for processing such a computationally large model using suitable mathematical processing techniques that allow the model to be processed in a reasonable amount of time without losing necessary detail. The invention addresses these and other needs in the art.

SUMMARY

The above and other needs in the art are addressed using a digital method for creating a tooth model using a statistical technique whereby the resulting tooth model can be modified in a way that maintains a natural tooth shape. The invention does not rely on a specific statistical technique, but may use the math of k-means clustering or principal component analysis (PCA) to analyze the tooth model. The invention modifies these methods to add detail to the resultant tooth model without complicating the mathematical analysis. In an exemplary embodiment, k-means clustering has been adapted into a technique that can be used to create a tooth model with minimal degradation of the results.

Those skilled in the art will appreciate that statistical approaches such as PCA or k-means clustering can be mathematically manipulated to substitute the smooth parameters with a full featured set. For example, the simplest way to do this with the PCA approach is to take the resulting model, subtract out an average tooth shape and add back in a full featured model. On the other hand, the k-means clustering approach builds its model by including a representation of the average model that can be accessed directly in the calculation, which is quite smooth compared to a natural sample. Then k-means clustering adds the dominant features back into the resulting model for a more natural look. It is those less important aspects that give fine detail to the resulting model. These fine details are mostly random across the input samples. As such, it makes no difference which "random" set of details to use to make a resulting tooth look natural. With this background, the inventors have discovered that by replacing the de-featured average model in the PCA or k-means clustering mathematical models with details from any of the teeth in the input sample, that the resulting statistical model retains all of the important structural aspects of the model, while also providing a fine detailed appearance to the model that does not impact the important aspects of the resulting model.

Exemplary embodiments of the invention include a method for creating a tooth model using a statistical technique such that the resulting tooth model can be modified in a way that maintains a natural tooth shape. For example, such a method may include the steps of:

scanning samples of a single tooth type into 3D format;

for each set of single tooth type scanned samples, determining a set of common points across all single teeth in the sample;

performing a statistical analysis of the data in the sample teeth using the common points to create an average statistical model of each tooth position;

replacing the average statistical model of a tooth position with a tooth sample having surface details for the tooth position; and performing a statistical combination of at least a portion of the tooth sample having surface details and structures of the statistical model for a tooth top of interest.

In accordance with the invention, the statistical analysis is performed using a k-means clustering algorithm or a principal component analysis algorithm. The resulting statistical model for a tooth top of interest may be used to create a deformable tooth model for use in visualizing restorative dental anatomy during the creation of a patient specific dental restoration. Interactive crown design may be performed using the statistical combination of at least a portion of the tooth sample having surface details and structures of the statistical model for the tooth top of interest.

Embodiments of the invention also include the steps of controlling sharpness of the statistical model for the tooth top of interest by adjusting an amount of surface detail interactively on a continuous scale between 0% and 100% and interpolating a result between a "no details" and "full details" based on the scale value. These and other embodiments of the invention will become apparent from the following detailed description.

BRIEF DESCRIPTION OF THE DRAWINGS

Exemplary embodiments of the invention will be described in conjunction with the associated figures, of which.

DETAILED DESCRIPTION OF ILLUSTRATIVE EMBODIMENTS

Certain specific details are set forth in the following description with respect to FIGS. 1-8 to provide a thorough understanding of various embodiments of the invention. Certain well-known details are not set forth in the following disclosure, however, to avoid unnecessarily obscuring the various embodiments of the invention. Those of ordinary skill in the relevant art will understand that they can practice other embodiments of the invention without one or more of the details described below. Also, while various methods are described with reference to steps and sequences in the following disclosure, the description is intended to provide a clear implementation of embodiments of the invention, and the steps and sequences of steps should not be taken as required to practice the invention.

When building a statistical shape model from a number of samples of an element of anatomy, it is typical to subtract the average shape of the training samples from the original data set and apply the statistical model to the "de-trended" data set. The same approach is adopted by the inventors in building a statistical crown model from 3D tooth samples (e.g. 100) per tooth type. In this fashion, an arbitrary 3D tooth shape can be reconstructed based on a linear combination of components (eigenvectors in the PCA model or clusters of averages in the k-means approach) added to the average of the tooth samples. Typically, the average shape is very smooth due to the combined variations in all tooth samples and the fact that the reconstructed tooth shape does not contain enough "sharpness" or surface details when only the first N (e.g., N=30) principal components or k-means cluster samples are used for performance reason to adjust the model interactively. To address this issue in accordance with the invention, the tooth shape is enhanced in accordance with the invention by providing more anatomical details to the statistical crown model. In particular, the original average tooth model is replaced with a similar tooth sample in overall shape and size but with more surface details. Consequently, the final tooth shape reconstructed by the enhanced average model retains the full anatomical details while capturing important variations in the tooth shape by a relatively small number of principal components or cluster averages.

Surface details may be added to the tooth model as follows:

1. In an offline pre-processing step, take a standard tooth model with full surface details for each tooth type and deform its overall structure to match the average model of the statistical tooth model without affecting surface details using any 3D geometry processing software. Save both the deformed detailed model and statistical average model for interactive crown design processing.

(Steps 2-5 are during interactive crown design process)

2. A tooth model that results from the underlying statistical structure is presented to the user.

3. The user sets a desired sharpness level (0%-100%) for the presented statistical model.

4. A deviation vector is computed by subtracting the average model from full detailed model, multiplied by the sharpness factor (=sharpness level/100).

5. The deviation vector is either added to the (global) average model (for PCA) or to each cluster average (for k-means clustering) to compute the final model to be presented back to the user.

In an exemplary embodiment, the invention thus includes the steps of creating a statistical model of a tooth using an existing statistical model (e.g., k-means clustering or principal component analysis) and then, in an off-line method, replacing the average tooth shape in the model with the full-featured model. The modeling software would then apply the statistical model to the full-featured model to generate and display the resulting tooth shape with increased detail.

Figure 1:
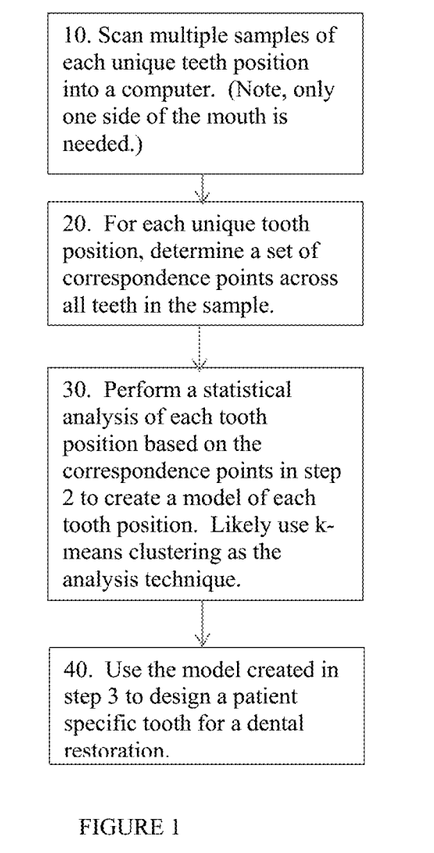
FIG. 1 illustrates the general steps of a k-means clustering approach for generating a statistical tooth model in accordance with an embodiment of the invention.

By way of example, the statistical model may be generated using a PCA technique of the type described by Mehl and others as noted above. On the other hand, a k-means clustering model for modeling a tooth is not readily available and thus has been developed by the inventors. In such a k-means clustering embodiment, a digital method for creating a tooth model using a statistical technique is provided such that the resulting tooth model can be modified in a way that maintains a natural tooth shape. As shown in FIG. 1, the general steps of a k-means clustering approach includes the following steps:

1. Scan samples of a single tooth type into a 3D format suitable for computer processing (step 10). The number of scanned samples needs to be large enough to show representative variation in that tooth type. In practice, the inventors used 100 samples. Even though there are 32 tooth positions, it is noted that tooth models only need to be created for the 16 teeth on one side of the mouth. The system can rely on bilateral symmetry to create the other 16 tooth models.

2. For each set of single tooth type scanned samples, determine a set of common points across all single teeth in the sample (step 20). These correspondence points are used to correlate features across the teeth samples as input to the statistical model.

3. Perform a statistical analysis of the data in the sample teeth using the correspondence points from step 2 to create a statistical model of each tooth position (step 30). In step 30, a k-means clustering technique is used in an exemplary embodiment, as described further below. However, those skilled in the art will appreciate that this step could also be performed using a PCA approach or other statistical processes such as those described in the background above that apply to 3D structure analysis.

4. Perform a statistical combination of at least a portion of the resulting statistical structures for the tooth top of interest (step 40). In the case of k-means clustering, it is noted that this step would be satisfied by a weighted linear combination of cluster averages. In PCA, on the other hand, this step would be satisfied by a weighted combination of principal components.

In an exemplary embodiment, the step of determining a set of common points across all single teeth in the sample involves using a "Harmonic Map" to build correspondence across multiple 3D objects. One of most important and challenging steps in creating a PCA, k-means cluster, or any other statistical analysis based 3D object model is to build a full point-to-point correspondence across multiple training samples of the target object type (e.g., molar teeth). Based on a well-known technique called "Harmonic Map" as described by Kanai et al. in an article entitled "Three dimensional geometric metamorphosis based on harmonic maps," The Visual Computer 14, 4(1998), 166-176, the inventors applied harmonic maps in a novel way to compute the point-to-point correspondence across multiple tooth samples of the same tooth type, combined by manual feature (landmark) selection and the scattered data interpolation method as described by Pighin et al. in an article entitled "Synthesizing realistic facial expressions from photographs," Proceedings of SIGGRAPH 1998, 75-84.

In an exemplary embodiment, the steps of determining common points across all single teeth in the sample include:

1. Selecting a small number of important dental features (e.g. cusp points) across all N sample objects manually per tooth type.

2. Creating a harmonic map as described in the Kanai et al. article, which maps 3D triangle meshes to 2D unit disks.

3. Selecting a reference object in the sample set and overlaying the harmonic map of a target object on the harmonic map of the reference object.

4. Moving all feature points (obtained in step 1) of the target object to the position of the corresponding feature points of the reference object and moving the rest of the points accordingly based on the scattered data interpolation technique as described in the Pighin et al. article.

5. For all points in the reference object, finding the triangle on the interpolated harmonic map of the target object and computing the barycentric coordinate of the point in the triangle, which can be used to locate the corresponding 3D position of the original target 3D object.

Once the common points are so identified, in the statistical analysis step 3, both the PCA and k-means clustering approaches start off by measuring and recording information about some variable data into a computer model. If measuring a human face, for example, that data might include the position of the center of the eyes, the edge of the eyes, the total height and width of the head, the position of the mount vertically, and the position of the corners of the mouth. In practice, there are many more common reference points of data, typically as many reference points as there are data points in the image of each face. The result is a set of data points about each of some number of different faces. The same approach applies to a tooth except that the data relates to features of the tooth.

Figure 2:
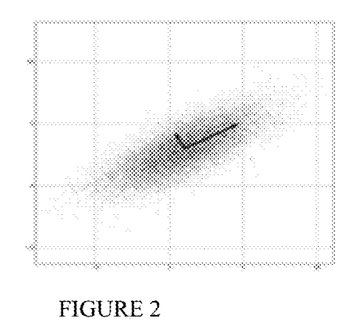
FIG. 2 illustrates PCA vectors in connection with a graph plotting just 2D points in an x-y graph.

Both k-means clustering and PCA are used to make a statistical model of how these various data points change across the input data of all the faces, but they do this in very different ways. PCA makes a model of how all that data changes across all the faces. FIG. 2 illustrates a graph plotting just 2 points in an x-y graph. It will be appreciated that this relates to not just x and y data but includes a dimension for each of the data points collected. FIG. 2 is simplified to two dimensions as that is easier to see in a diagram. PCA looks for the direction where the data is most variable. In FIG. 2, that direction is the same as the long arrow. Notice how it is sloped in relation to the x-y direction. That direction is the most important "component" of change in the data set. In other words, it is the "principal component" of the data. In fact, it is the first principal component of the data. The 2nd principal component is the narrower direction at a right angle to the first (in math, it is orthogonal, which means that changes in that direction are independent of changes in the other direction). Note, that if many more data points were illustrated, not just the two shown, then there would be a principal component for each of them.

In PCA, the components lack a certain physical meaning. In the original data space, the x and y positions have meaning like the height of the center of the right eye, and the distance of the center of the right eye from the middle of the face. However, the principal component does not have as clear a physical meaning. In PCA space, humans are really only able to get a sense of the meaning of these dimensions. For the face example, the principal vector may be thought of as representing something like the position of the right eye in relation to the width of the left nostril.

Those skilled in the art will appreciate that by selecting any point in the PCA space, one can translate back to positions in the original data space (the x-y, or eye positions) and get a face that matches the inputs. Moreover, as one gets further down the list of principal components, the amount of variability in the data goes way down, and it becomes unnecessary to do the math on the further down components to get a really good likeness to the face one is trying to create. In the face example, a lower component might represent the position of the 3456th hair follicle over the upper lip. If that moves, the face will still look like the same person. This allows the math to be performed much more quickly and retain all the important parts of the face, which is the principal benefit of using PCA.

Figure 3:
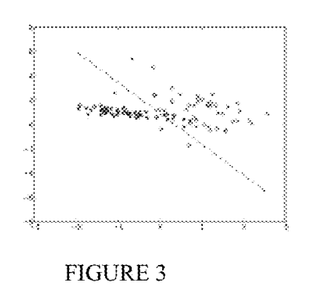
FIG. 3 illustrates k-means clustering in connection with data points illustrated as a cluster of darker data in darker points.

As will now be explained, k-means clustering also accomplishes a reduction in data processing but in a different way. What k-means clustering does is look for patterns in the data where sets of data points "cluster" in similar ways. Also, while PCA is applied to deviations from the average of the data set, k-means clustering is applied directly to the data set. FIG. 3 shows a cluster of darker data in darker points. The math of k-means clustering breaks the data into some number of sets (the math uses the letter "k" to say how many of these sets one is going to look for). Then the data is evaluated for the best way to break the data into these k sets such that the sum of distances from each data point to its cluster average (or more technically, the "mean") is the smallest possible. It is noted that the system does not look for just the smallest distance to the cluster means for each set but rather looks for the set where all the "distances" are added together so as to have the smallest value. In other words, the system is looking for a specific set of "k" "clusters" with the lowest sum of distances to the cluster means. After these clusters have been found, any specific data set can be represented as having some amount of fit to each of the independent k-means clusters, which allows these factors to be combined to reconstruct a specific data set that corresponds to the combination of a specific set of k-means. In k-means clustering, variability to the "mean" point is being reduced for each cluster to simplify the math.

In PCA, one could have as many principal components as there are sample points in the dataset. However, the system is designed to ignore the points that do not vary that much. In k-means clustering, on the other hand, one can have as many clusters as desired up to the number of points in the dataset (again). Complexity is reduced by representing each cluster of data by a single point, its mean. Essentially, all the data is ignored and only the set of "means" is used instead of the actual data. Both methods have the property that they allow one to reduce the complexity of the input data. Both methods also have the property that they can be converted back to some data that is in the range of the training data. However, they accomplish these tricks by very different mathematical approaches.

Those skilled in the art will appreciate that PCA and k-means clustering are not variants of each other but are instead completely different mathematical constructs with the same end (reducing data complexity) in mind.

Once the statistical crown model is created using PCA or k-means clustering, a statistical combination of at least a portion of the resulting statistical structures for the tooth top of interest is performed that supports interactive change of the crown model. Although a statistical shape model captures important variations in the training samples, those skilled in the art will appreciate that it is not trivial to interpret the axes of variations captured in the principal components or cluster averages. In other words, it is not easy to create a desired object shape interactively out of the statistical model by adjusting the weight of each eigenvector or cluster average manually. Due to this nature of the statistical shape model, its use is mostly focused on the automatic reconstruction or shape matching based on additional information (e.g., photographs in the afore-mentioned Blanz article). However, since it is desired to make use of a statistical crown model in order to design crowns interactively according to the customer-specific dentition environment, a method has been further developed to interpret an interactive change of a control point in the model surface into an optimal set of weights of the eigenvectors or cluster averages of the underlying statistical model. The steps of the method include:

1. A set of control points corresponding to important dental features are pre-determined in the statistical crown model.

2. The user changes one of the control points on the presented model surface interactively.

3. The surface of the presented model is deformed based on the interactive change using scattered data interpolation as described in the Pighin et al. article.

4. (For PCA-model only) The average of the PCA-model is subtracted from the deformed surface, which is called the deviation vector.

5. (For PCA-model) The deviation vector is multiplied by the transpose of the matrix composed by the column space of the N eigenvectors and added to the average of the PCA-model. The resulting vector is the optimal set of N weights of corresponding eigenvectors in a least square sense. (For k-means clustering model) A set of weights of cluster averages is computed using a non-negative least square method, that would fit to the deformed model (computed in step 3) in an optimal way with the given constraints.

6. The crown shape reconstructed with the computed weights in step 5 represents a best matching crown shape (in the statistical model) to the deformed shape created by the interactive change in step 3.

As noted above, the statistical combination is satisfied for PCA by a weighted combination of principal components. On the other hand, in the case of k-means clustering, this step is satisfied by a weighted linear combination of cluster averages.

Adding Surface Detail Using a Full Featured Example

Those skilled in the art will appreciate that in computer graphics it is important to keep the underlying geometry of the 3D object as simple as possible to achieve fast rendering and animation. There are various known techniques to create the "effects" of detailed surfaces with a simple geometry such as "bump mapping" (FIG. 5), which is frequently used in video game systems. Most of these techniques are used to achieve visual effects by perturbing the surface normal during the rendering process without changing the underlying object.

As another example, Blanz et al. describe in "A morphable model for the synthesis of 3D faces," Proceedings of SIGGRAPH 99, pages 187-194, August 1999, a method to reconstruct a 3D face from a single photograph using the face model acquired by performing Principal Component Analysis (PCA) for multiple samples of human faces. Blanz et al. perform the PCA in the geometry space (i.e. positions of surface points) and texture space (i.e. colors of the surface points) separately. However, the reconstructed texture based on the suggested method lacks the details in the input photographs due to the inherent limitation of PCA. To compensate for this problem, Blanz et al. extracted the actual texture from the input photograph and blended it into the synthesized texture from the PCA.

While such techniques also propose to add surface details to the underlying 3D model, several key differences exist with respect to the methods described herein. For example, the method described herein is applied to the "geometry" (i.e., 3D surface points) directly—not in the texture or surface normal, and the method described herein actually changes the underlying 3D object without adding more surface points. In addition, the method described herein provides a single canonical form of detailed information per object type that is applied to every reconstructed model. In other words, only one instance of (pre-computed) detailed information is required per tooth type. Such a method works well especially for certain types of subjects (such as teeth) where the difference in actual details is not very important as long as it follows the correct anatomy of the specific tooth type that the model represents. Applicants note that this assumption may not be true for some object types such as human faces where minor details may make important differences.

PCA and k-Means Clustering

Both a PCA method and k-means clustering method can be used to reduce the dimensionality of a large-scale multivariate dataset in efficient (but different) ways. PCA is an eigenvector analysis against the covariance matrix of the de-trended dataset (i.e. deviation from the average, which is often referred as "mean centering"). The resulting eigenvectors are orthogonal to each other and can be ordered by the magnitude of the corresponding eigenvalues to represent axes of variation of the dataset in the order of their importance (i.e. amount of variation). Therefore, after performing the PCA of N data points of dimensionality M, one gets the N−1 eigenvectors and the first k eigenvectors ($u_i$) can be combined linearly to reconstruct an arbitrary new data point as in the following equation:

$$p = F(\alpha) = \bar{c} + \sum_{i=0}^{k} \alpha_i u_i \quad (1)$$

where $\alpha$: weight vector, c: average model, $u_i$: ith eigenvector

Figure 6:
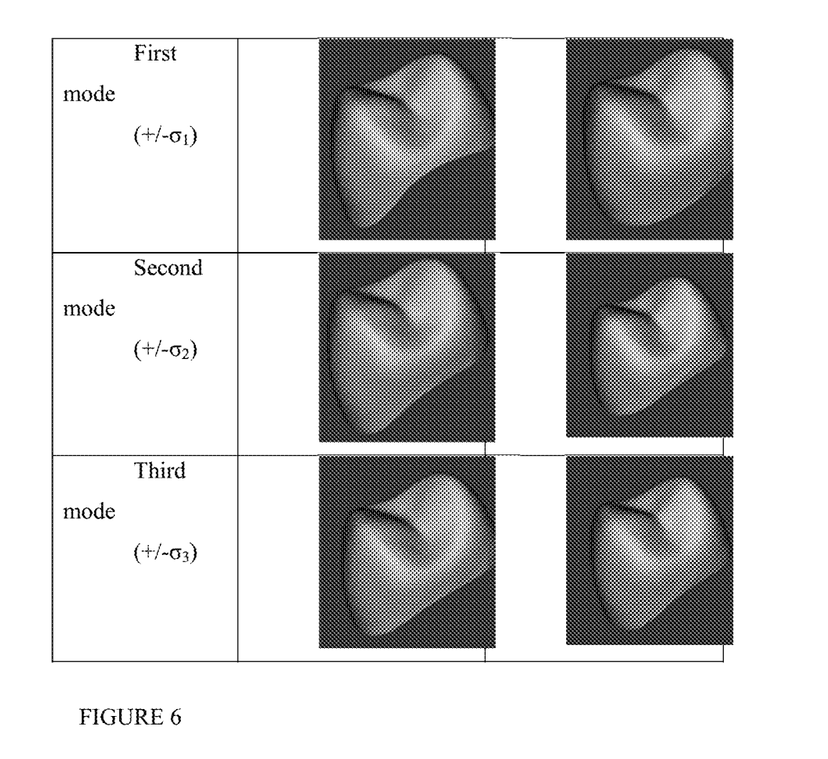
FIG. 6 illustrates an example of applying PCA to 40 different samples of bicuspids (tooth #5).

FIG. 6 shows an example of applying PCA to 40 different samples of bicuspids (tooth #5). The three rows represent the three largest variations of the samples captured by the first three principal components (multiplied by the square root of the corresponding eigenvalues (+/−σ1). The probability of the weight vector (coefficients $\alpha$) is given by:

$$p(\alpha) = \exp\left[-\frac{1}{2}\sum_{i=1}^{k}(\alpha_i/\sigma_i)^2\right]$$

So, when one reconstructs an arbitrary tooth using Equation (1), regularization on the resulting tooth shape can be achieved by limiting the range of coefficients based on the square root of the eigenvalues (e.g. $-3\sigma_i \leq \alpha_i \leq 3\sigma_i$).

k-means clustering is another tool for multivariate data analysis especially for cluster analysis in data mining, which has a completely different historical path and typically different application area than PCA. k-means clustering aims to partition N data points of dimensionality M into k different clusters based on the similarity of each data point against other data points in the samples. The inventors have observed that this grouping (or clustering) of similar shape of samples together provides another statistically effective way of reducing the amount of data to represent an arbitrary 3D object based on the multiple observations of the same object type. In one extreme, one can represent an arbitrary model by the linear combination of all samples, which is most demanding computationally but most expressive. In the other extreme, one can represent an arbitrary model by the average of all samples, which is least demanding computationally but least expressive. In between, one can represent an arbitrary model by the linear combination of the average of each cluster after clustering the dataset into k groups based on the similarity of its members, which could be less demanding computationally if k is relatively small compared to N, but without sacrificing expressiveness much if the members of each cluster have very similar shapes to each other.

The following equation can be used to reconstruct an arbitrary object using the k cluster centers (or cluster means) obtained by k-means clustering method.

$$p = F(\alpha) = \sum_{i=0}^{k} \alpha_i c_i \quad (2)$$

where $\alpha$: weight vector, $c_i$: ith cluster center

In terms of regularization or the likelihood of the weight vector ($\alpha$), the obvious constraints should be:

$$0 \leq \alpha_i \leq 1, \quad (3)$$

$$\sum_{i}^{k} \alpha_i = 1$$

It is often required to find an optimal set of coefficients (α) that can represent an arbitrary object (p), which can be done by solving the set of linear equations (2) in the least square sense. However, in order to force the constraints on Equation (3), one cannot use the typical least square solver for this purpose. Instead. it is desired to apply a specific method called to solve this non-negative least square (NNLS) problem. Furthermore, the inventors have observed that applying NNLS on strictly positive constraints often yields a bit less optimal solution than allowing a small amount of negative values. For example, the inventors have observed that changing the constraints (3) to (4) often finds better solutions.

$$\varepsilon \le \alpha_i,$$
$$\varepsilon < 0,$$
$$\sum_i^k \alpha_i \lambda = \lambda,$$
$$\lambda \ge 1$$
(4)

To be able to apply the same NNLS algorithm on constraints (4), original least square problem is modified as follows:

$$\begin{bmatrix} p' \\ \lambda(1-\varepsilon k) \end{bmatrix} = \sum_{i=0}^{k} \alpha'_i \begin{bmatrix} c_i \\ \lambda \end{bmatrix},$$
$$\alpha'_i = \alpha_i - \varepsilon, \; p' = p + \sum_{i=0}^{k} \varepsilon c_i$$
(5)

where λ is a parameter that can be used to control how much emphasis to put on the second part of the constraint of (4). In an exemplary embodiment, the inventors found typically ε≈2 and λ≈2.0 provided the best results.

Sharpness of Image

In another exemplary embodiment of the invention, the sharpness of the resultant image may be controlled using the full-featured statistical model. In particular, the amount of surface detail is controlled using a sharpness control that allows the modeling software to move smoothly between the featured and less featured models. This approach allows the modeling software to simulate age and wear in a design.

Figure 4:
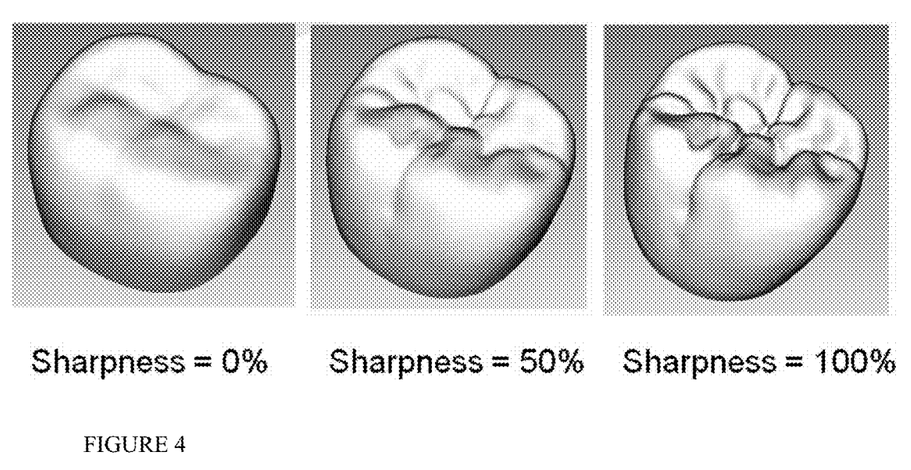
FIG. 4 illustrates varying sharpness provided by a sharpness control feature in accordance with the invention that allows users to adjust the amount of surface details interactively during the crown design process.
Figure 5:
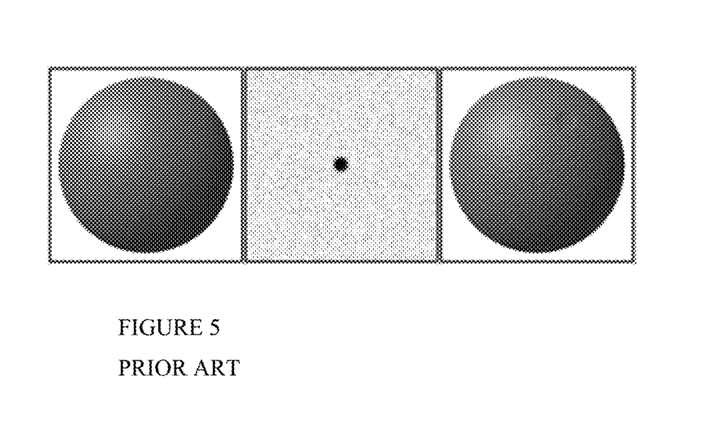
FIG. 5 illustrates "bump mapping" as used in conventional graphics applications.

A sharpness control feature in accordance with the invention allows users to adjust the amount of surface details interactively during the crown design process. The control provides a continuous scale between 0% and 100%, interpolating the result between the "no details" and "full details" based on the scale value, as shown in FIG. 4. The detailed mathematical equation to achieve this effect could be different based on the underlying statistical model of the crown.

For a PCA-Based Model:

$$p = F(\alpha, s) = \bar{c} + \sum_{i=0}^{k} \alpha_i u_i + s\delta$$

For k-Means Clustering-Based Model:

$$p = F(\alpha, s) = \sum_{i=0}^{k} \alpha_i (c_i + s\delta)$$

where s: sharpness factor, c̃: full detailed model, c̄: average model

Figure 7:
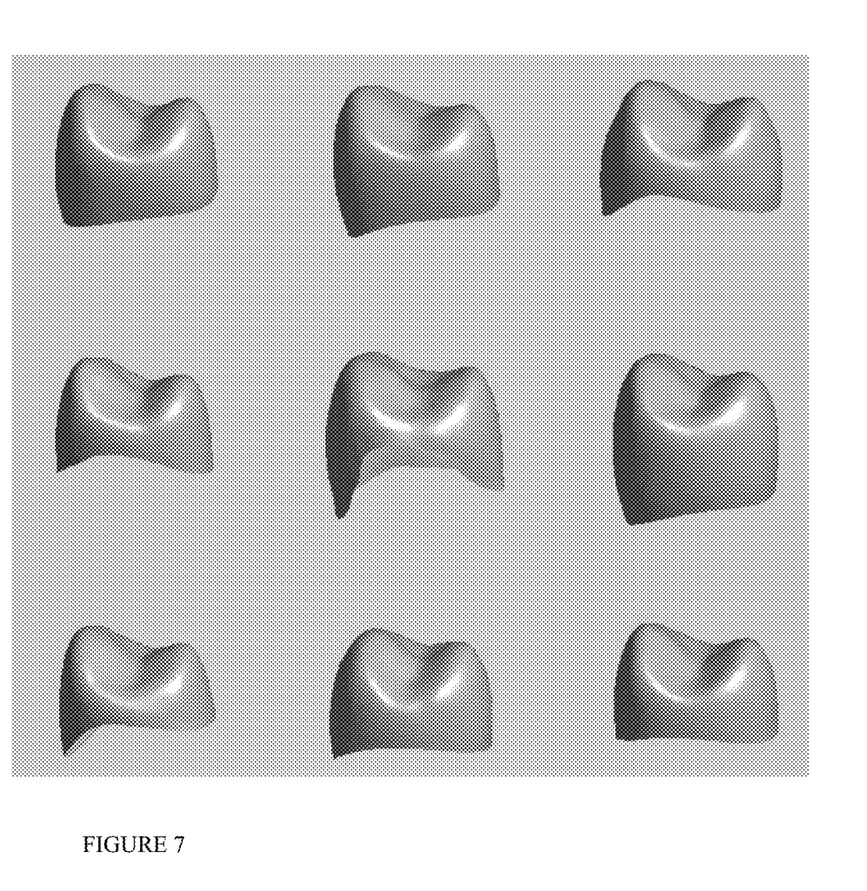
FIG. 7 illustrates an example of applying k-means clustering when k=9 for 101 bicuspid (#5) tooth samples.

FIG. 7 shows an example of applying k-means clustering when k=9 for 101 bicuspid (#5) tooth samples. Each tooth in the picture represents a cluster center (i.e. the average of each cluster) and an arbitrary tooth can be created by a linear combination of these cluster centers.

Figure 8:
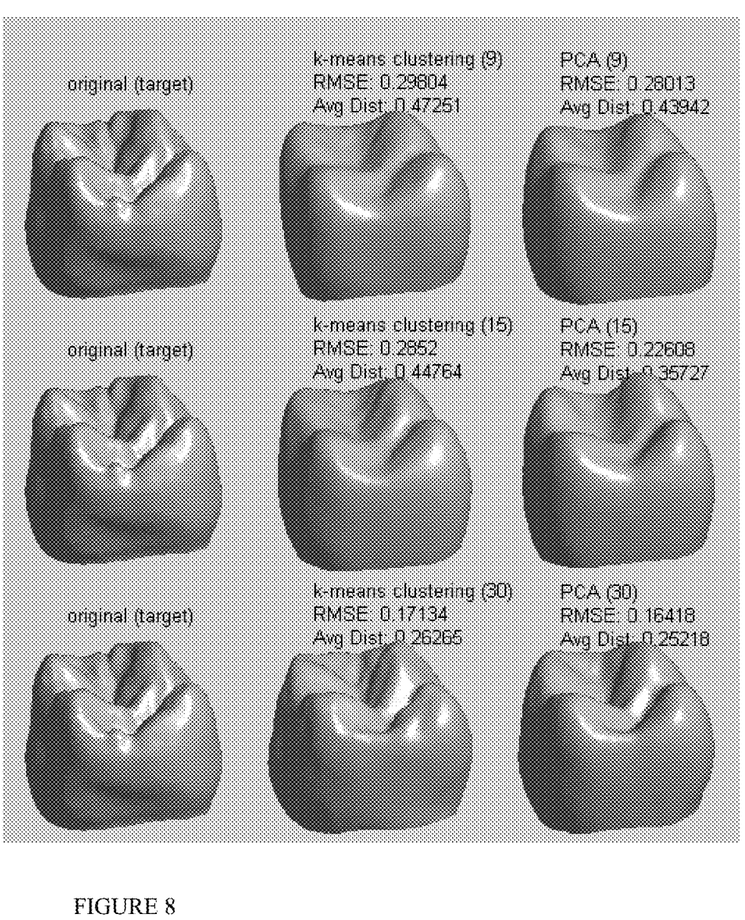
FIG. 8 illustrates the comparison between PCA and k-means clustering on how accurately each model can reconstruct an arbitrary (unknown) tooth model.

FIG. 8 shows the comparison between PCA and k-means clustering on how accurately each model can reconstruct an arbitrary (unknown) tooth model. Each row in FIG. 8 represents the reconstruction results with a specific number of bases (9, 15 or 30; which means the number of clusters for k-means clustering and the number for principal components for PCA) alongside the target tooth geometry to reconstruct.

Those skilled in the art will appreciate that the techniques described herein add value to dentistry by enabling the creation of a more aesthetic crown for patients. Those skilled in the art also will readily appreciate that many additional modifications and scenarios are possible in the exemplary embodiments without materially departing from the novel teachings and advantages of the invention. Accordingly, any such modifications are intended to be included within the scope of this invention as defined by the following exemplary claims.

What is claimed:

1. A method for creating a tooth model using a statistical technique such that the created tooth model is modified in a way that maintains a natural tooth shape, comprising:
    obtaining data representing a set of sample teeth by scanning samples of a single tooth type into a 3D format;
    for each set of single tooth type scanned samples, determining a set of common points across all single teeth in the samples;
    performing a statistical analysis of the data in the set of sample teeth using the set of common points to create an average statistical model of each tooth position; the statistical analysis is performed using a k-means clustering algorithm or a principal component analysis (PCA) algorithm;
    replacing the average statistical model of a tooth position with a tooth sample having surface details for the single tooth type; and
    performing a statistical combination of at least a portion of the tooth sample having surface details and structures of the average statistical model of the tooth position for a tooth top of interest,
    the method further including:
    deforming said tooth sample to match the average statistical model of the tooth position;
    determining a sharpness level for use on the deformed tooth sample wherein said sharpness level is between 0% and 100%;
    computing a deviation vector by subtracting the average statistical model of the tooth position from the deformed tooth sample, multiplied by a sharpness factor, wherein said sharpness factor is the sharpness level/100; and
    adding the deviation vector to the average statistical model of the tooth position when the statistical analysis is performed using the PCA algorithm or to cluster averages when the statistical analysis is performed using the k-means clustering algorithm, in order to create the tooth model.

2. The method as in claim 1, further comprising using the average statistical model of the tooth position for the tooth top of interest to create a deformable tooth model for use in visualizing restorative dental anatomy during a creation of a patient specific dental restoration.

3. The method as in claim 1, further comprising using the average statistical model of the tooth position for the tooth top of interest to create a deformable tooth model for use in creating a physical patient-specific dental restoration.

4. The method as in claim 1, comprising performing interactive crown design using said statistical combination of at least the portion of the tooth sample having surface details and structures of the average statistical model of the tooth position for the tooth top of interest.

5. The method as in claim 4, wherein the statistical combination is satisfied for when the statistical analysis is performed using the PCA algorithm by a weighted combination of principal components.

6. The method as in claim 4, wherein the statistical combination is satisfied for when the statistical analysis is performed using the k-means clustering algorithm by a weighted linear combination of cluster averages.

7. The method according to claim 1, wherein determining the set of common points across all single teeth in the samples comprises computing point-to-point correspondence between respective teeth in the samples using a harmonic map.

\* \* \* \* \*